(12) United States Patent
Huet et al.

(10) Patent No.: US 9,743,936 B2
(45) Date of Patent: Aug. 29, 2017

(54) SURGICAL OSTEOTOMY METHOD, A METHOD OF CONTROL OF A COMPUTER PILOTED ROBOT AND A SURGICAL SYSTEM FOR IMPLEMENTING SUCH A SURGICAL METHOD

(71) Applicant: OSTESYS, Plouzane (FR)

(72) Inventors: Pierre-Yves Huet, Locmaria-Plouzane (FR); Stephane Lavallee, St. Martin D'uriage (FR)

(73) Assignee: MINMAXMEDICAL, La Tronche (FR)

( * ) Notice: Subject to any disclaimer, the term of this patent is extended or adjusted under 35 U.S.C. 154(b) by 570 days.

(21) Appl. No.: 14/203,771

(22) Filed: Mar. 11, 2014

(65) Prior Publication Data
US 2015/0257838 A1    Sep. 17, 2015

(51) Int. Cl.
| | |
|---|---|
| *A61B 17/00* | (2006.01) |
| *A61B 17/16* | (2006.01) |
| *A61B 34/32* | (2016.01) |
| *A61B 17/80* | (2006.01) |
| *A61B 34/30* | (2016.01) |
| *A61B 34/00* | (2016.01) |
| *A61B 34/10* | (2016.01) |

(Continued)

(52) U.S. Cl.
CPC .......... *A61B 17/16* (2013.01); *A61B 17/8095* (2013.01); *A61B 34/10* (2016.02); *A61B 34/20* (2016.02); *A61B 34/30* (2016.02); *A61B 34/32* (2016.02); *A61B 34/76* (2016.02); *A61B 2017/1602* (2013.01); *A61B 2017/681* (2013.01); *A61B 2034/102* (2016.02); *A61B 2034/105* (2016.02); *A61B 2034/107* (2016.02); *A61B 2034/108* (2016.02); *A61B 2034/2055* (2016.02); *Y10S 901/41* (2013.01)

(58) Field of Classification Search
CPC combination set(s) only.
See application file for complete search history.

(56) References Cited

U.S. PATENT DOCUMENTS

| | | | |
|---|---|---|---|
| 2010/0291505 A1* | 11/2010 | Rawley | A61C 13/0004 433/72 |
| 2015/0182236 A1* | 7/2015 | Dardenne | A61B 17/17 606/281 |

* cited by examiner

*Primary Examiner* — Sameh Boles
(74) *Attorney, Agent, or Firm* — Blakely Sokoloff Taylor & Zafman LLP

(57) ABSTRACT

The invention relates to a surgical method of attachment of a first bony segment in relation with a second bony segment, both segments belonging to a same bone, which comprises the steps of:
  milling said bone and cutting it partially, to separate it in two bony segments linked together by a bony hinge
  distracting both bony segments around said hinge;
  fitting an osteotomy implant into the cavity thus obtained;
  attaching said implant to both bony segments;
wherein it comprises the preoperative steps of:
  determining the position and the direction of the future partial cut, calculating its depth, calculating the relative three-dimensional positions of both bony segments to obtain the final desired alignment of the two bony segments,
  choosing among several osteotomy implants, one which is wider than the largest distance between the facing sides of said bony segments after distraction,
  determining the position and the shape of the future implant reception cavity and calculating its dimensions,
  deducing therefrom the shape of the two part cavities to be milled in the bone before the distraction step.

11 Claims, 5 Drawing Sheets

(51) Int. Cl.
 *A61B 34/20* (2016.01)
 *A61B 17/68* (2006.01)

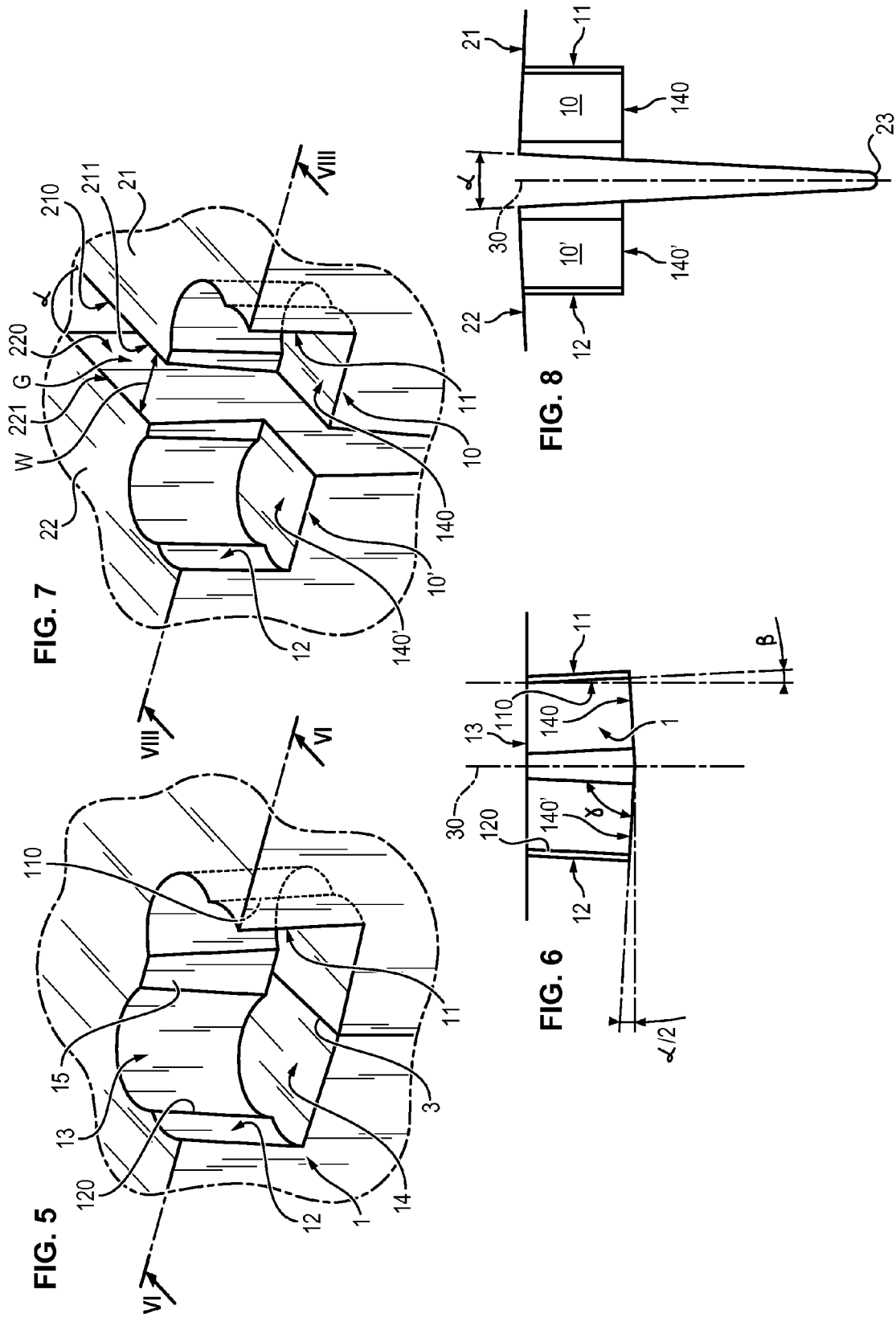

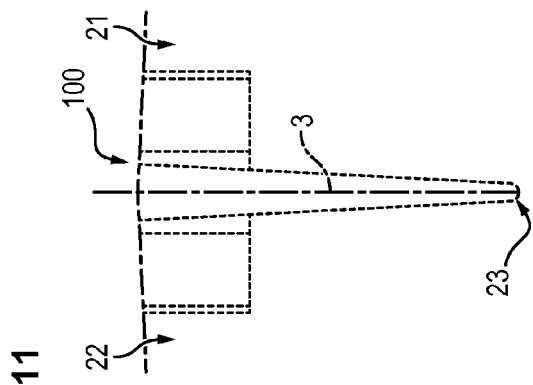
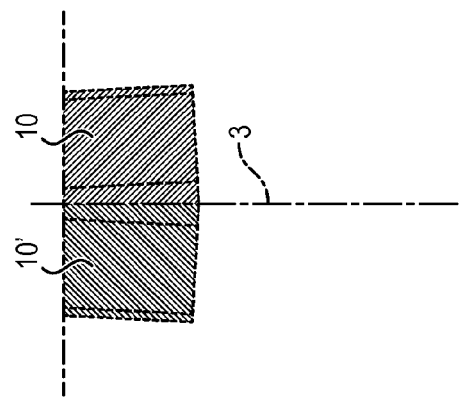
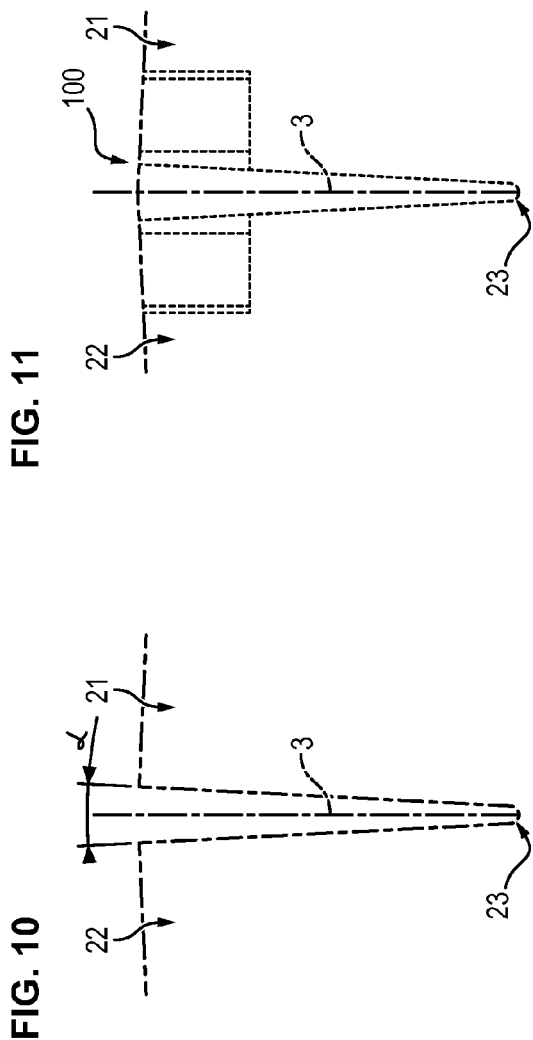
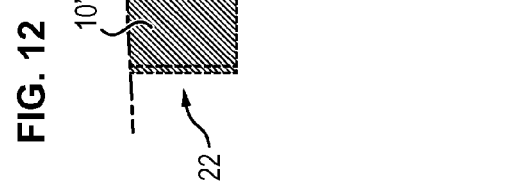
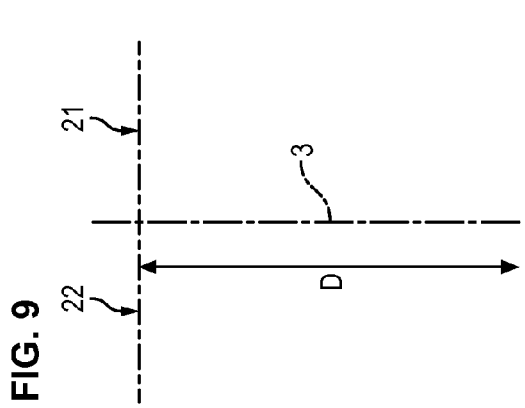

SURGICAL OSTEOTOMY METHOD, A METHOD OF CONTROL OF A COMPUTER PILOTED ROBOT AND A SURGICAL SYSTEM FOR IMPLEMENTING SUCH A SURGICAL METHOD

BACKGROUND

Field of the Invention

The present invention relates to a surgical method of attachment of a first bony segment in relation with a second bony segment, both segments belonging to a same bone, for osteotomies, and to a method of control of a computer piloted robot and a surgical system for implementing such kind of surgical method.

Description of Related Art

Osteoarthritis is a mechanical abnormality involving degradation of the joints, including articular cartilage and subchondral bone.

This pathology can be treated using different methods. The most common one is the total replacement of the diseased joint with a prosthetic implant. This method is however very degenerative, invasive and sometimes traumatic for the patient.

When this disease is the consequence of a misalignment of a limb, it can be delayed or treated with an opening osteotomy. This surgical procedure aims to rebalance the stress on the diseased joint by realigning the joint centers of the limb (hip, knee and ankle centers for the lower limb and shoulder, elbow and wrist for the upper limb). A partial cut is thus performed on one of the two bones forming the limb (femur or tibia for the lower limb, and, humerus or radius for the upper limb). The deformation is made by rotating the cut bones around a rotation point called "hinge" resulting from the partial cut. Once the alignment has been reached, the two cut bony segments are maintained in the desired position, in most cases, with an osteosynthesis implant.

The Arthrex Company commercializes an osteotomy implant comprising two longitudinal faces, each one being provided with two curved areas spaced apart from each other with a central flat area between them.

To put in place such an implant, the surgeon drills two spaced apart holes in the bone, and then he cuts the bone along the diameter of the two holes, then inserts the implant inside the opening after having distracted the two bony segments and finally fixes it with screws. This implant maintains the relative positions of the two bony segments and avoids the over-thickness of conventional osteotomy plates.

Nevertheless, this way of operating has several drawbacks:
- the resulting alignment can be inaccurate and can lead to bad post-operative results since the required correction angle to align the lower limb is planned preoperatively in simple two-dimensions (2D) x-rays and is reported during the surgery with a simple geometric ruler;
- the system cannot adjust the alignment of the limb in the three required rotations of the space. Only the alignment in the frontal plane can be realized, the slope (rotation in the sagittal plane) and the coronal rotations cannot be correctly adjusted which can lead also to non-optimal postoperative results;
- the surgeon needs to have a large number of implants of different sizes to choose among them the most appropriate to the size and the shape of the hole obtained after distraction of the two bony segments, (ideally one implant per degree or half-degree of opening wedge);
- the surgeon may even have some difficulties to find an implant perfectly matching with the hole particularly when the performed hinge does not create a perfect opening axis after distraction;
- there is also the risk that the implant enters too deeply between the two bony segments.

SUMMARY

It is an object of the present invention to provide a surgical method for the attachment of two bony segments belonging to a same bone, which allows the surgeon to adjust and maintain these two segments with a higher accuracy than the method of the prior art.

Another object of the invention is to implement this surgical method by using a limited number of implants of different sizes.

Accordingly, the invention provides a surgical method of attachment of a first bony segment in relation with a second bony segment, both segments belonging to a same bone, which comprises the following steps of:

a) milling said bone and cutting it partially, the cutting step being implemented until obtaining a partial cut which separates partially said bone in two bony segments linked together by a bony hinge and the milling step being implemented in order to create a cavity extending between a top face forming an opening in the bone surface and a bottom face opposite to the top face, both steps being implemented such that said partial cut separates said cavity into two part cavities, b) distracting said first bony segment with respect to said second bony segment around said hinge until obtaining a desired three-dimensions alignment of the two bony segments and reaching a position in which facing sides of said bony segments are separated from each other by a predetermined opening angle α;

c) fitting an osteotomy implant into the cavity obtained after distraction named "implant reception cavity" until reaching the bottom face of said two part cavities;

d) attaching said implant to both of said first and second bony segments;

wherein before step a), the surgical method comprises the following preoperative steps of:
- determining the position and the direction of the future partial cut, calculating its depth, calculating the future opening angle α and the relative three-dimensional position of the first bony segment with respect to said second bony segment necessary to obtain the final desired alignment of the two bony segments,
- choosing among several osteotomy implants, one which is wider than the future largest distance between the respective top edges of the facing sides of said bony segments after distraction,
- determining the position and the shape of the future implant reception cavity with respect to the future partial cut and calculating the dimensions of said future implant reception cavity,
- deducing therefrom the shape of the two part cavities to be milled in the bone before the distraction step b).

Thanks to these features of the invention, the cavity created in the bone is adapted to better match with the implant and the resulting fixation of the two bony segments is more accurate. Therefore the resulting alignment of the limb is also improved.

Further since the bone is milled and cut to match with the implant, it is possible to use (and thus to store) a small number of implants.

According to other advantageous and non-limiting features of the invention, taken alone or in combination:
- said milling step is implemented by using a computer piloted robot whose working head is able to be moved according to at least three degrees of freedom, the working head supporting a milling tool;
- said cutting step is implemented by using a computer piloted robot whose working head is able to be moved according to at least three degrees of freedom, the working head supporting a cutting tool;
- the computer piloted robot is a haptic robot;
- the milling step is done before the cutting step;
- the milling step is done after the cutting step;
- in step a), the milling of said cavity is implemented with a cylindrical milling tool so as to create, in the opposite longitudinal faces of the cavity, a plurality of parallel concave surfaces extending from the top face to the bottom face, wherein each concave surface is a portion of a cylindrical surface having the same diameter as the diameter of the cylindrical milling tool;
- step c) is implemented by using an implant whose longitudinal faces have a shape which is complementary to the shape of the opposite longitudinal faces of said cavity once the first and second bony segments are distracted;
- in step a), the cutting of said bone is implemented until obtaining a partial cut which separates said cavity in two half part cavities which are the image of one another with reference to said plane;
- in step a), the milling of said cavity is implemented in order to create in the bone an elongated cavity having two opposite longitudinal faces diverging from each other from the top face to the bottom face of the cavity, the angle between each longitudinal face and the plane of the partial cut being positive and less than or equal to α/2.

Another object of the invention is to provide a method of control of a computer piloted robot for implementing at least some steps of the previous surgical method.

Accordingly, the invention provides a method of control of a computer piloted robot having a working head that is able to be moved according to at least three degrees of freedom, in order to implement a surgical method of attachment of a first bony segment in relation with a second bony segment, both segments belonging to a same bone, which comprises the hereunder steps:
- when a milling tool is coupled to the working head, causing said milling tool to mill a hollow cavity in the bone, while positioning said working head and said milling tool until obtaining an elongated cavity having two opposite longitudinal faces diverging from each other from the top face to the bottom face of the cavity;
- when a cutting tool is coupled to the working head, causing said cutting tool to cut partially said bone until obtaining a partial cut which separates partially said bone in two bony segments linked together by a bony hinge, and which separates said cavity into two part cavities.

Another object of the invention is to provide a surgical system for implementing a surgical method of attachment of a first bony segment in relation with a second bony segment, both segments belonging to a same bone, the system comprising:
- a robot having a working head that is able to be moved according to at least three degrees of freedom and to be configured so as to receive each one of a milling tool and a cutting tool;
- a control computer configured to:
  - i/ compute and register in real time the position of said tool with respect to the position of said bone;
  - ii/ when the tool attached to the working head is said milling tool, control said milling tool for milling in said bone a cavity extending between a top face forming an opening in the bone surface and a bottom face opposite to the top face;
  - iii/ when the tool attached to the working head is the cutting tool, control said cutting tool so as to cut partially said bone in two bony segments linked together by a bony hinge, and which separates said cavity in two part cavities,
- a computer configured to preoperatively:
  - determine the position and the direction of the future partial cut, calculating its depth, calculating the future opening angle α and the relative position of the first bony segment with respect to said second bony segment necessary to obtain the final desired alignment of the two bony segments,
  - choose among several osteotomy implants, one which is wider than the largest distance between the respective top edges of the facing sides of said bony segments after distraction,
  - determine the position and the shape of the future implant reception cavity with respect to the future partial cut and calculating the dimensions of said future implant reception cavity,
  - deduce therefrom the shape of the two part cavities to be milled in the bone before the distraction step.

According to other advantageous and non-limiting features of the invention, taken alone or in combination:
- the robot is a haptic robot;
- the milling step is done before the cutting step;
- the milling step is done after the cutting step;
- the milling of said cavity is implemented with a cylindrical milling tool so as to create, in the opposite longitudinal faces of the cavity, a plurality of parallel concave surfaces extending from the top face to the bottom face, wherein each concave surface is a portion of a cylindrical surface having the same diameter as the diameter of the cylindrical milling tool.

BRIEF DESCRIPTION OF THE DRAWINGS

Other characteristics and advantages of the invention will become apparent from the description which will now be given with reference to the appended drawings, which by way of indication but in non-limiting manner illustrate various variants of possible embodiments of the invention.

In the drawings:

FIG. 5 is a partial perspective schematic view of the hollow cavity milled in a bone, before cutting and distraction of the two bony segments, FIG. 6 is a cross-sectional view taken along the line VI-VI of FIG. 5, FIG. 7 is a partial perspective schematic view of the hollow cavity milled in a bone, after cutting and distraction of the two bony segments, and FIG. 8 is a cross-sectional view taken along the line VIII-VIII of FIG. 7, FIGS. 9 to 13 are schematic views illustrating the different postoperative steps of the surgical method of the invention.

DETAILED DESCRIPTION OF A PREFERRED EMBODIMENT

The different steps of a first embodiment of the surgical method will now be described in relation with the FIGS. 1 to 4.

Figure 1:
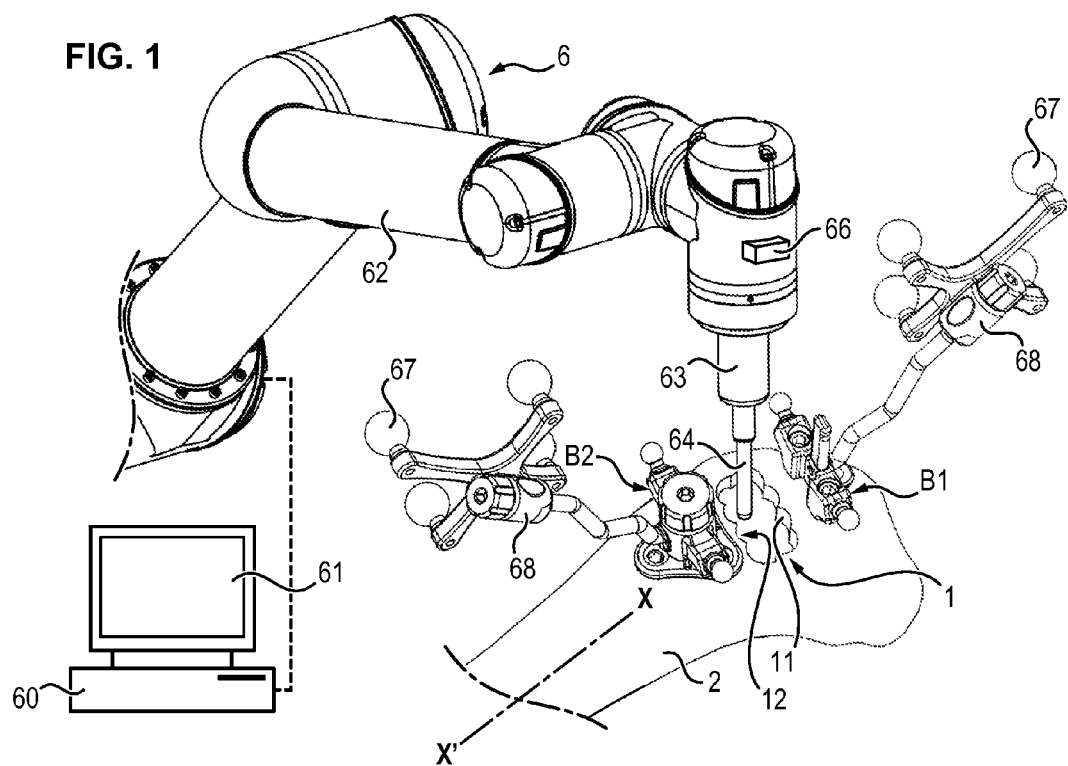
FIGS. 1 to 4 show different steps of the surgical method according to the invention, and FIGS. 1 and 2 also show a part of the surgical system used to implement this method.

As can be seen on FIG. 1, a hollow cavity 1 is milled in a bone 2.

Preferably, before starting the method, two bases B1 and B2 are fixed onto the bone 2 on each side of the future cavity. Different tools or trackers can be attached to said bases.

This cavity 1 has preferably an elongated shape with two opposite longitudinal faces 11 and 12 extending in a transverse or approximately transverse direction with respect to an axial direction X-X of the bone 2. The hollow cavity 1 extends between a top face 13 defining an opening in the surface of the bone 2 and a bottom face 14 opposite to the top face 13 (see FIG. 5).

Subsequently the bone 2 is partially cut according to a cut plane 30 (sectional plane) represented on FIG. 6, which has a transverse or approximately transverse direction with respect to an axial direction X-X' of the bone until obtaining a partial cut 3, (see FIG. 2).

The partial cut 3 separates partially the bone 2 in two bony segments 21, 22 linked together by a bony hinge 23 which is visible on FIG. 8. Further, the partial cut 3 also separates the hollow cavity 1 into two part cavities 10, 10'.

Preferably these two part cavities 10, 10' are the two halves of the hollow cavity 1 and each one is the image of the other with reference to the cut plane.

Figure 14:
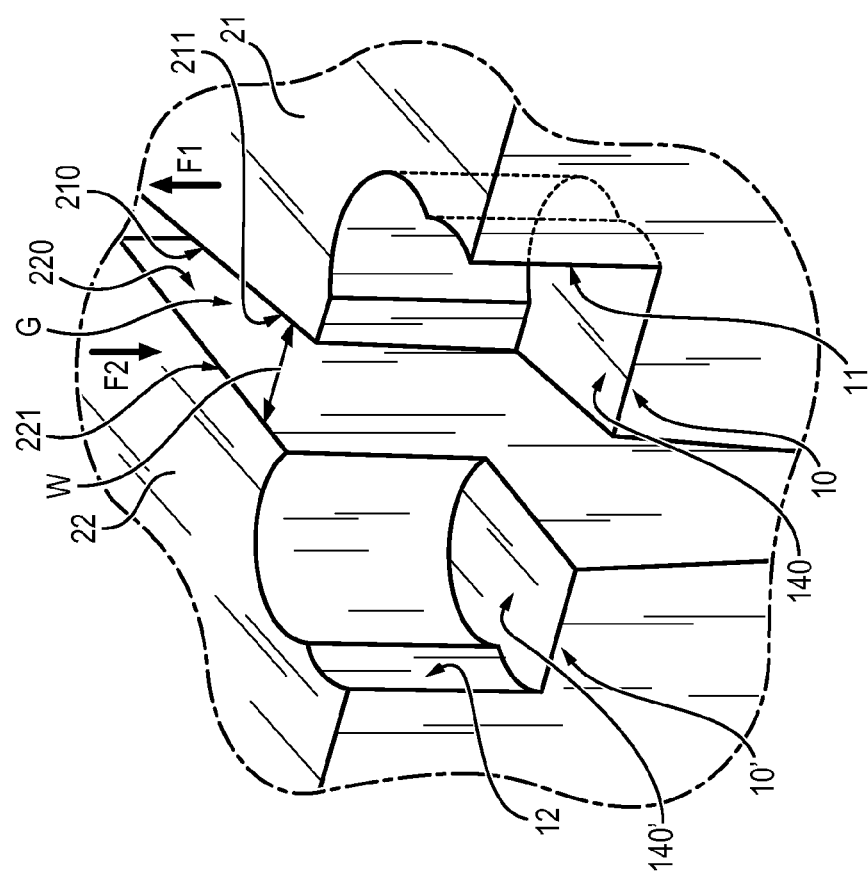
FIG. 14 is a partial perspective schematic view of the hollow cavity representing a situation different from the one of FIG. 7.

Nevertheless, sometimes it may be different as represented on FIG. 14 and explained later in more details.

The fact of milling the cavity 1 before cutting the bone is advantageous because the bone is more resistant before the cutting step.

Nevertheless, according to a second embodiment of the invention it is also possible to realize the cutting step before the milling step.

Figure 3:
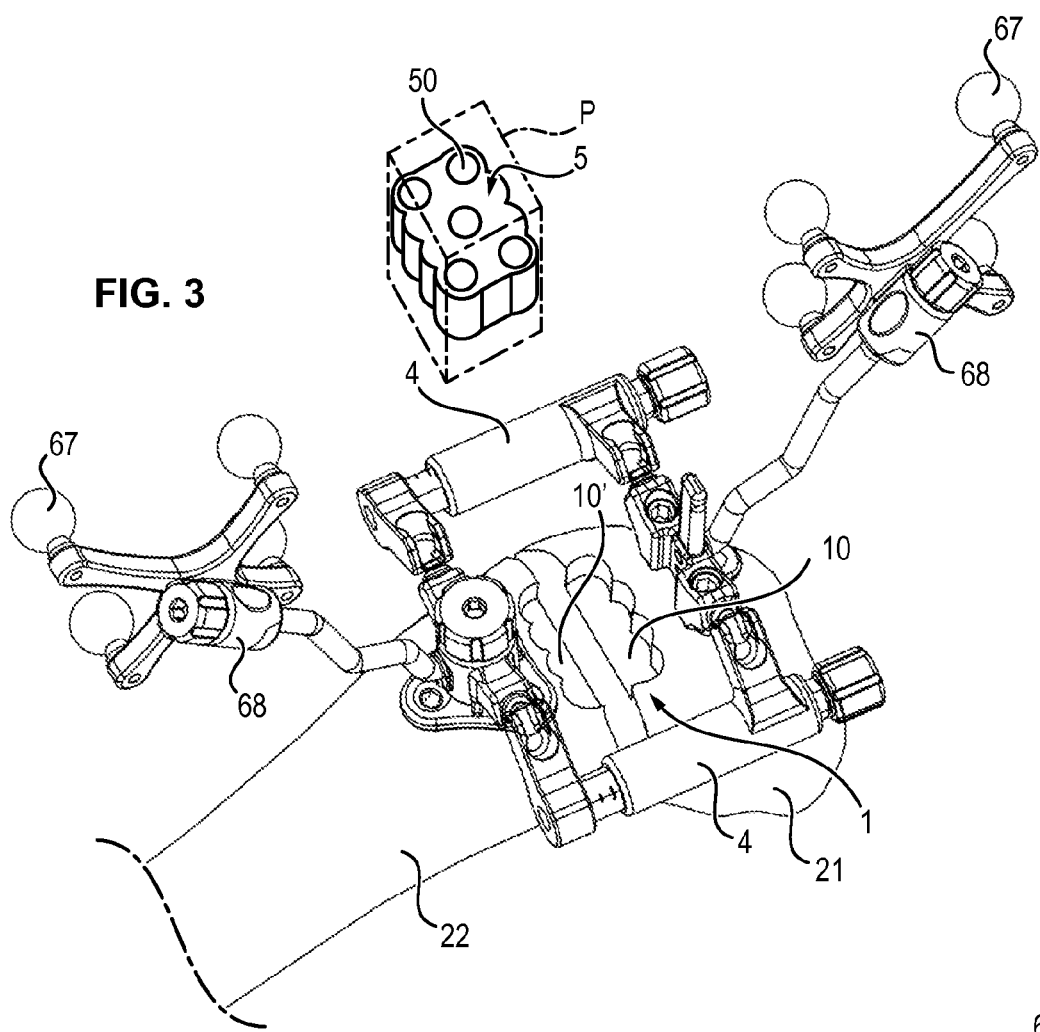

Thereafter and as can be seen on FIG. 3, the first bony segment 21 and the second bony segment 22 are distracted (i.e. spaced apart) around said hinge 23, for example by using spacers 4. The spacers 4 are preferably attached to the bases B1 and B2 and maintain the distraction of both bony segments.

In the distracted position, the facing sides 210, 220 of the respective bony segments 21, 22 are separated from each other from an angle α, see FIGS. 7 and 8. Preferably and typically, the angle α is comprised between 5° and 15°.

Figure 4:
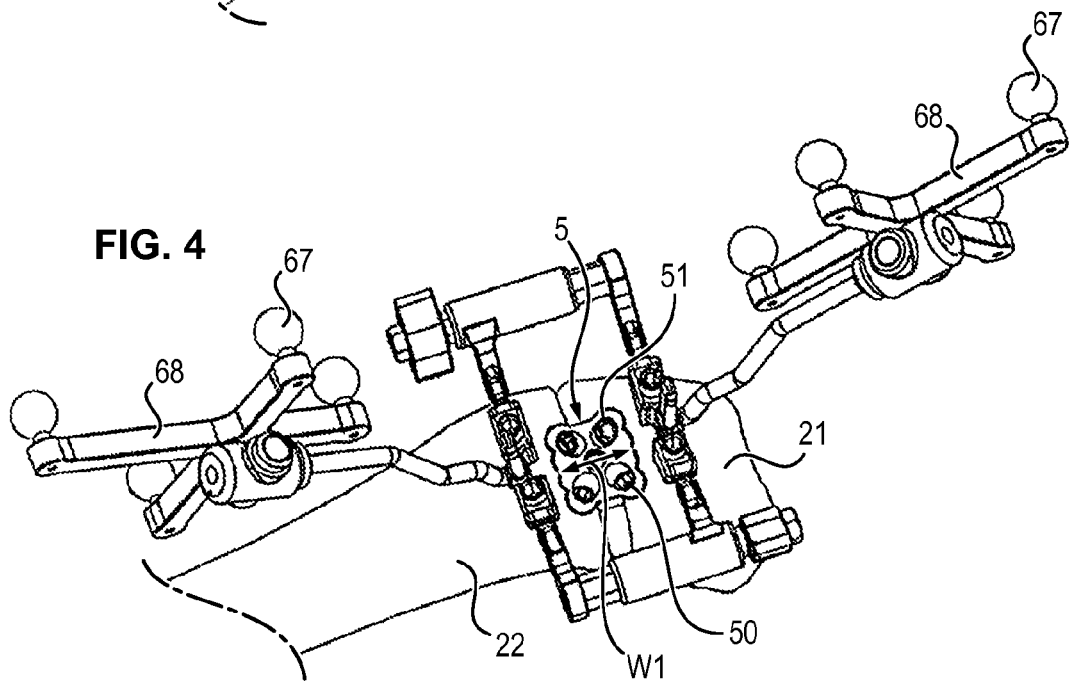

Finally, as shown on FIG. 4, an osteotomy implant 5 is fitted into the hollow cavity 1 until it reaches the bottom faces 140, 140' of the respective two part cavities 10, 10'. The implant 5 is attached to both bony segments 21, 22. Preferably, the implant 5 is provided with several holes 50, for example four holes and is screwed in the bone 2 by using screws 51.

According to the invention, before to implement the previously described surgical steps, some preoperative steps are realized, preferably by using a computer (not shown on the figures).

As above-mentioned the aim of an opening osteotomy is to realign the joint centers of the limb (hip, knee, ankle centers for the lower limb and shoulder, elbow and wrist for the upper limb).

On the basis of several preoperative medical images and data (x-rays echography, . . . ), the surgeon knows for example the pathologic angle HKA (Hip-Knee-Ankle) or SEW (Shoulder, Elbow, Wrist) of his patient.

On the basis of these data, the computer can compute the desired alignment of the two bony segments. To obtain this desired alignment, the computer will then determine the position, the direction and the depth of the future partial cut 3, the angle α of the hinge 23 after distraction of the bony segments 21, 22 and the relative three dimensional positions of the first bony segment 21 with respect to said second bony segment 22.

The position of the hinge 23 is important to create a desired rotational axis. The depth D is also important to obtain a hinge that is small enough to be easy to open and distract without the necessity to generate very strong forces that could lead to breaking the hinge, and large enough to keep enough bone material such that the hinge will resist to shear and stretch forces during opening and distraction, also to prevent breaking.

Figure 15:
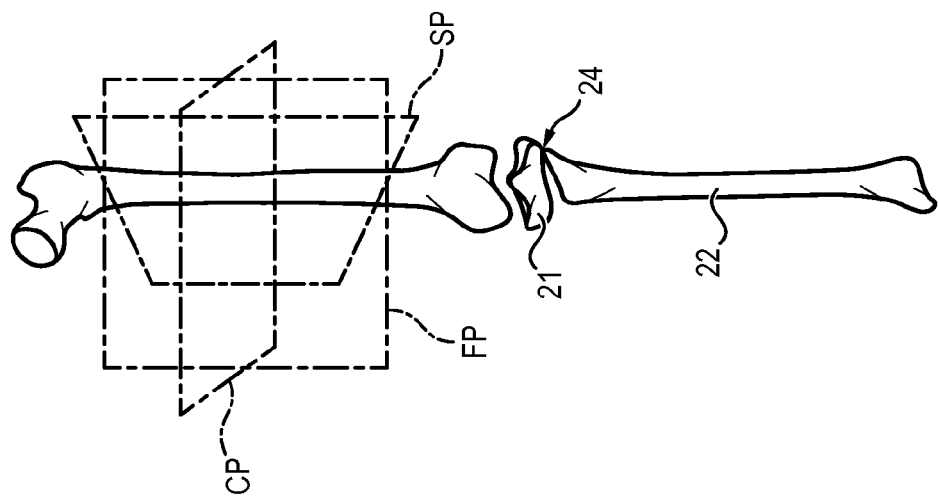
FIG. 15 is a schematic view representing two tibial bony segments, a femur and the anatomical reference system.

Typically a value of nine millimeters for the remaining part 24 of the hinge can be selected by the surgeon, but it can be also adapted to each patient individually according to the bone size and density (see FIG. 15). The bony hinge can be defined with respect to one or several points acquired with a sharp pointer, tracked by the same localizer as the robot, on the bone transcutaneously, at the opposite side of the surgical site.

It is to be noted that the hinge 23 is flexible enough to allow some additional degrees of freedom. Therefore if necessary, the two bony segments 21, 22 are not only spaced apart one from the other but may also be slightly rotated one with respect to the other. If necessary, the two bony segments 21, 22 may be distracted in the frontal plane FP, in the sagittal plane SP and in the coronal plane CP as can be seen on FIG. 15.

FIG. 7 represents the situation where the tow bony segments 21, 22 are spaced apart from a gap G of constant width W. FIG. 14 represents the situation where the gap G is of increasing width W. Further the two bony segments may be slightly titled one from the other (arrows F1, F2). In this case, the two part cavities 10, 10' are not the image of one another and cavity 10' is smaller than cavity 10.

The computer can also compute the width W if it is constant or the medium width if it is increasing.

The computer can choose, among several (preferably a small number of) osteotomy implants (for example small, medium, large), one of appropriate size, particularly one of appropriate width W1, wider than the largest future distance between the respective top edges 211, 221 of the facing sides of the two bony segments 21, 22.

Then, the computer determines the position and the shape of the future implant reception cavity 100, i.e. the cavity after distraction, with respect to the future partial cut 3 and calculates the dimensions of said future implant reception cavity (see FIG. 11).

As can be seen on FIG. 12, the future implant reception cavity 100 is constituted of the two part cavities 10, 10' plus the central cavity 10" obtained after the distraction of the two bony segments 21, 22 and extending between said two part cavities 10, 10'.

Finally, the computer computes preoperatively the global shape and the dimensions of the two part cavities 10, 10' to be milled in said bone 2 before the distraction step (see FIG. 13). Thus after the distraction, the chosen osteotomy implant 5 matches perfectly with the cavity obtained, i.e. the two part cavities 10, 10' and the gap G between the two bony segments 21, 22. One possible embodiment of the shape of the hollow cavity 1 will now be described in more detail.

Preferably, the milling (reaming) of the hollow cavity 1 is implemented with a cylindrical milling tool (for example a drill) so as to create along each of the longitudinal faces 11, 12, a plurality of portions of a cylindrical surface having the same diameter as the diameter of said cylindrical milling tool. The portions of the cylindrical surfaces of the longitudinal faces 11, 12 are contiguous and two contiguous portions are separated by an edge 110, respectively 120.

The edges 110, 120 improve the locking of the implant 5 inside the cavity 1.

The cavity 1 has also two opposite lateral faces 15, 16 (end faces).

The longitudinal faces 11 and 12 are diverging from each other from the top face 13 to the bottom face 14 of the cavity 1.

Preferably, as can be seen on FIG. 6, the angle β between the cut plane 30 and each longitudinal face 11 or 12 (or one of its edges 110 or 120) is positive and less than or equal to α/2, more preferably equal to α/2 (i.e. the half of the angle α separating the facing sides 210, 220 of the distracted bony segments 21, 22). On FIG. 6, said angle β is represented between the edge 110 and a plane parallel to the plane 30.

Thus, once the two bony segments 21 and 22 are distracted, as represented on FIG. 8, the longitudinal faces 11 and 12 of the hollow cavity 1 (or the edges 110 and 120) are parallel.

Preferably also, the bottom faces 140, 140' of the two part cavities 10, 10' are slightly inclined one toward the other (see FIG. 6). The angle γ between the cut plane 30 and each bottom face 140, 140' is preferably comprised between 90° minus a positive angle and 90° minus α/2, more preferably equal to 90° minus α/2 such that, after the distraction of the two bony segments 21 and 22, as represented on FIG. 8, their bottom faces 140, 140' are parallel and in the same plane.

Preferably, the value of the angles α, β, γ are determined prior to the implementation of the milling step.

The fact of milling the hollow cavity 1 with longitudinal faces diverging from each other, more particularly with an angle of half the one of the future angle of distraction a allows using osteotomy implants with parallel longitudinal faces or at least osteotomy implants whose shape is inscribed within a rectangular parallelepiped P with parallel longitudinal faces as can be seen on FIG. 3. Therefore it is no more necessary to store a large number of implants with different angles of slope of their longitudinal faces.

Preferably, some steps of the surgical method of the invention are implemented by using a surgical system comprising a computer piloted robot 6 and a control computer 60 to pilot this robot.

The control computer 60 includes a screen 61. The computer 60 comprises a memory in which is recorded a computer program and a treatment unit adapted to execute this program.

The fact of using a robot to perform the milling and the cutting steps is advantageous because of its high accuracy. The cutting guide and the milling guide used in the prior art techniques are less accurate.

Said robot can be a haptic robot moved by the surgeon and constrained by the computer such as the well-known RIO robot of the company MAKO SURGICAL. It can be also an active robot such as the well-known ROBODOC device. In both cases, one or both bone segments and the robot can be equipped with markers in order to check and compensate for relative motions of the robot basis with respect to the bone. On the example represented on FIGS. 1 and 2, the robot 6 comprises a swivel arm 62 provided with several axis of rotation and pivot axis offering at least three degrees of freedom (preferably six).

The data transfer between the robot 6 and the swivel arm 62 is realized by any suitable connection, with wires or wireless as represented by the dotted line. The robot can have any type of architecture, for example a serial architecture as indicated in the drawings, but also a parallel architecture as this of the well-known robot produced by the company MAZOR.

The robot is also provided with a working head 63 configured to receive tools, particularly a milling tool 64 with a drill and a cutting tool 65 with a cutting blade.

The data concerning the position and the depth of the future partial cut 3, the position, the shape and the dimensions of the hollow cavity to be milled are entered in the computer 60.

Preferably, the robot 6 is also provided with a 3D-localizer 66. The 3D-localizer may be of any type, for example an optical localizer, a magnetic localizer, an ultrasound localizer or an accelerometer.

Figure 2:
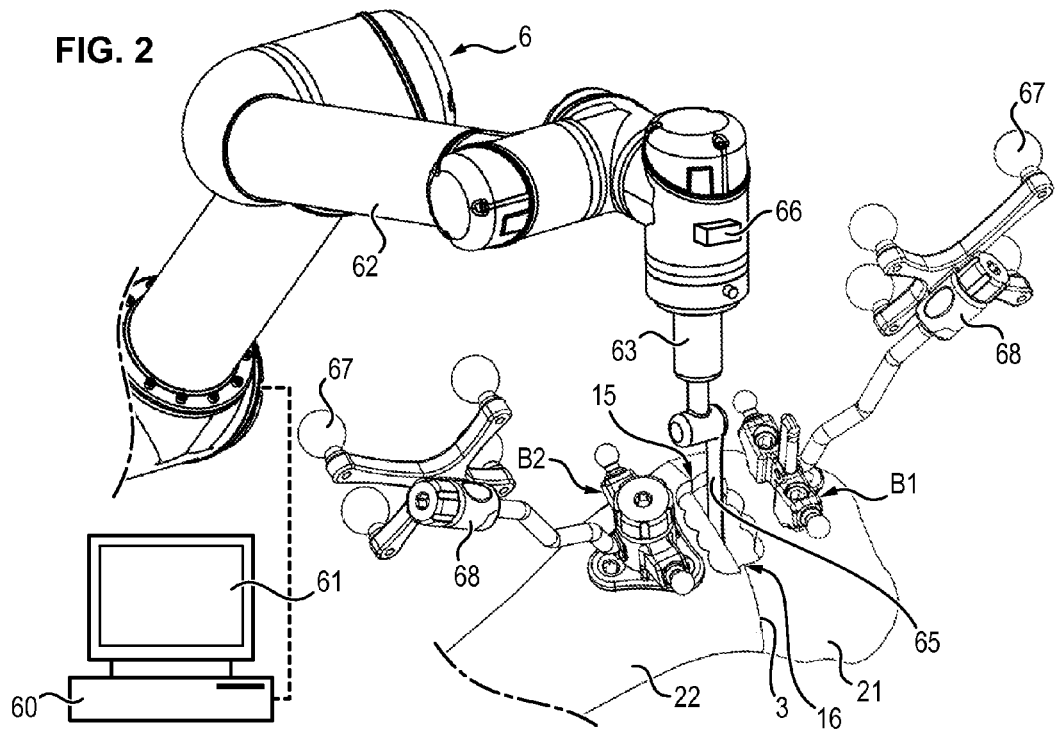

In the example represented on FIGS. 1 and 2, the 3D-localizer is an optical one. It is provided with a camera which can determine by triangulation the 3D-position of markers 67 disposed on trackers 68 fixed to the basis B1 and B2. Similar trackers are fixed to the bone.

The computer receives the data from the localizer and computes and registers in real time the position of the tool 64, 65 with respect to the position of the markers and thus the position of the bone 2.

When the tool attached to the working head 63 is the milling tool 64, the computer pilots the robot 6 and the swivel arm 62 for milling the hollow cavity 1 such as previously described.

When the tool attached to the working head 63 is the cutting tool 65, the computer pilots the robot 6 and the swivel arm 62 to realize the partial cut 3.

It is also possible to use a haptic robotic system including a computer and a hand held device that comprises a handle manipulated by the surgeon and bearing a milling tool or a cutting tool.

The computer pilots the robot to prevent the surgeon to move the milling tool outside of the desired hollow cavity or the cutting tool outside of the desired cutting plane and to prevent to saw the desired hinge (preserving its desired depth and position).

The robot is also able to detect a change in the position of the limb and the bone to be treated to adapt consequently the permitted movement of the milling or cutting tools.

The invention claimed is:

1. A surgical method of attachment of a first bony segment in relation with a second bony segment, both segments belonging to a same bone which comprises the following steps of:
 a) milling said bone and cutting it partially, the cutting step being implemented until obtaining a partial cut which separates partially said bone in two bony segments linked together by a bony hinge and the milling step being implemented in order to create a cavity extending between a top face forming an opening in the bone surface and a bottom face opposite to the top face, both steps being implemented such that said partial cut separates said cavity into two part cavities,
 b) distracting said first bony segment with respect to said second bony segment around said hinge until obtaining a desired three-dimensions alignment of the two bony segments and reaching a position in which facing sides of said bony segments are separated from each other by a predetermined opening angle α;

c) fitting an osteotomy implant into the cavity obtained after distraction named "implant reception cavity" until reaching the bottom face of said two part cavities;

d) attaching said implant to both of said first and second bony segments;

wherein before said milling, the surgical method comprises the following preoperative steps of:

determining the position and the direction of the future partial cut, calculating its depth, calculating the future opening angle α and the relative three-dimensional position of the first bony segment with respect to said second bony segment necessary to obtain the final desired alignment of the two bony segments, choosing among several osteotomy implants, one which is wider than the future largest distance between the respective top edges of the facing sides of said bony segments after distraction, determining the position and the shape of the future implant reception cavity with respect to the future partial cut and calculating the dimensions of said future implant reception cavity, deducing therefrom the shape of the two part cavities to be milled in the bone before said distracting.

2. The surgical method according to claim 1, wherein said milling step is implemented by using a computer piloted robot whose working head is able to be moved according to at least three degrees of freedom, the working head supporting a milling tool.

3. The surgical method according to claim 1, wherein said cutting step is implemented by using a computer piloted robot whose working head is able to be moved according to at least three degrees of freedom, the working head supporting a cutting tool.

4. The surgical method according to claim 1, wherein the computer piloted robot is a haptic robot.

5. The surgical method according to claim 1 wherein the milling step is done before the cutting step.

6. The surgical method according to claim 1 wherein the milling step is done after the cutting step.

7. The surgical method according to claim 1, wherein, in the milling step, the milling of said cavity is implemented with a cylindrical milling tool so as to create, in the opposite longitudinal faces of the cavity, a plurality of parallel concave surfaces extending from the top face to the bottom face, wherein each concave surface is a portion of a cylindrical surface having the same diameter as the diameter of the cylindrical milling tool.

8. The surgical method according to claim 7, wherein said fitting is implemented by using an implant whose longitudinal faces have a shape which is complementary to the shape of the opposite longitudinal faces of said cavity once the first and second bony segments are distracted.

9. The surgical method according to claim 1 wherein, in the milling step, the cutting of said bone is implemented until obtaining a partial cut which separates said cavity in two half part cavities which are the image of one another with reference to said plane.

10. The surgical method according to claim 1, wherein, in the milling step, the milling of said cavity is implemented in order to create in the bone an elongated cavity having two opposite longitudinal faces diverging from each other from the top face to the bottom face of the cavity, the angle between each longitudinal face and the plane of the partial cut being positive and less than or equal to α/2.

11. The surgical method according to claim 2, wherein the computer piloted robot is a haptic robot.

* * * * *